(12) United States Patent
Fassuliotis

(10) Patent No.: US 6,638,240 B2
(45) Date of Patent: Oct. 28, 2003

(54) SURGICAL SUCTION INSTRUMENT

(76) Inventor: Thomas M. Fassuliotis, 4085 Cochran Rd., Gainesville, GA (US) 30506

( * ) Notice: Subject to any disclaimer, the term of this patent is extended or adjusted under 35 U.S.C. 154(b) by 133 days.

(21) Appl. No.: 09/726,692

(22) Filed: Nov. 29, 2000

(65) Prior Publication Data

US 2002/0065482 A1 May 30, 2002

(51) Int. Cl.⁷ .................................................. A61M 1/00
(52) U.S. Cl. ........................................... 604/27; 604/19
(58) Field of Search ............................ 604/22, 35, 40, 604/43, 73, 119, 44, 121, 27, 19

(56) References Cited

U.S. PATENT DOCUMENTS

| 4,878,900 | A | * | 11/1989 | Sundt | .......................... | 604/119 |
| 6,048,339 | A | * | 4/2000 | Zirps et al. | ................. | 604/525 |
| 6,050,971 | A | * | 4/2000 | Garnier et al. | ................ | 604/43 |
| 6,086,554 | A | * | 7/2000 | Humphreys, Jr. et al. | .... | 604/27 |

* cited by examiner

*Primary Examiner*—Henry Bennett
*Assistant Examiner*—Nihir B Patel
(74) *Attorney, Agent, or Firm*—Joseph N. Breaux

(57) ABSTRACT

A surgical suction instrument that includes a handle, a surgical cavity insertion tube, and a suction tube attachment fitting. The suction tube attachment fitting is in connection with the surgical cavity insertion tube at a location below a mechanical connection of the surgical cavity insertion tube and the handle. In one embodiment, the surgical cavity insertion tube terminates at a lower suction tube tip end in multiple suction intake openings formed through the bottom and bottom side surfaces of the lower suction tube tip end and each in fluid communication with a tube passageway thereof. In another, the surgical suction instrument further includes a surgical cavity insertion tube adjustment mechanism in connection between the handle and the surgical cavity insertion tube to allow the user to adjust the position of the surgical cavity insertion tube with respect to the handle as desired.

1 Claim, 3 Drawing Sheets

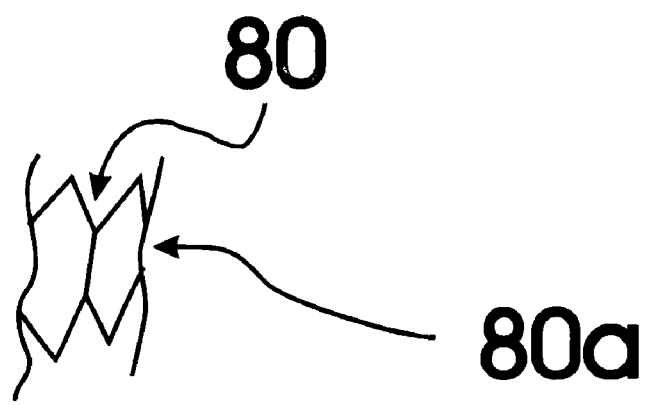
FIG.3
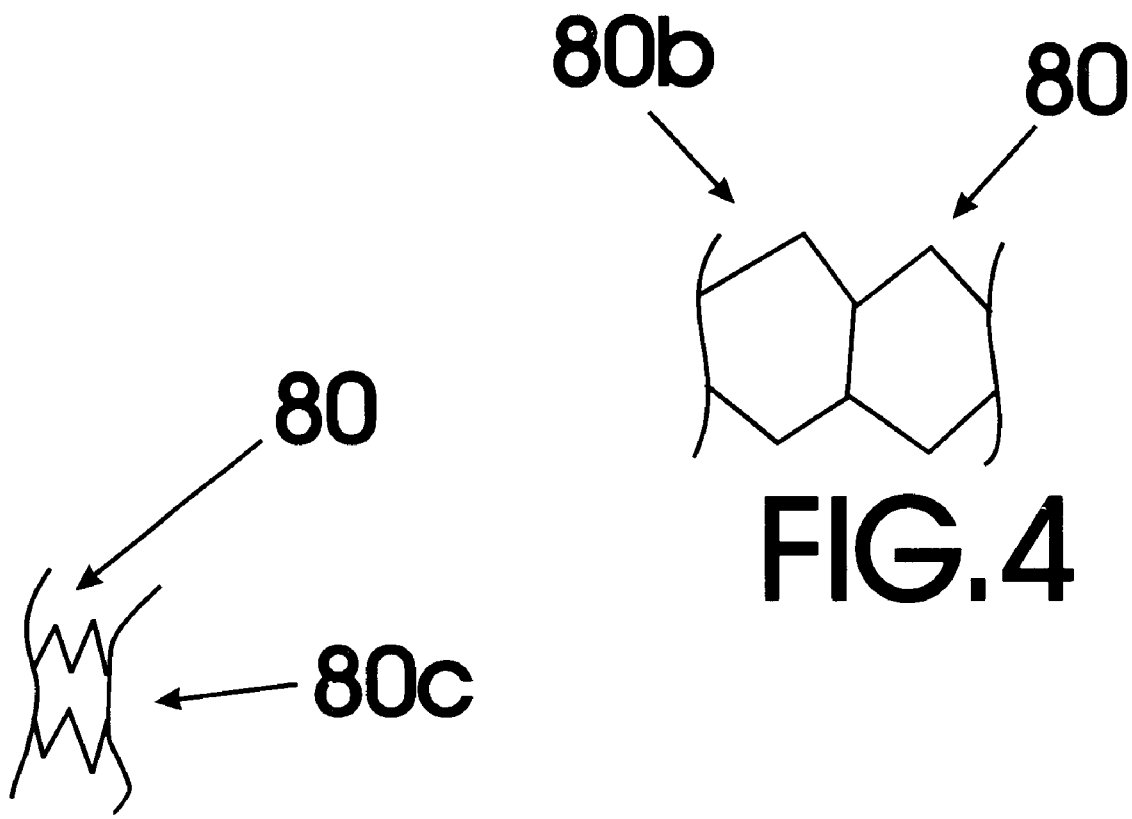
FIG.4
FIG.5

SURGICAL SUCTION INSTRUMENT

TECHNICAL FIELD

The present invention relates to surgical accessories and more particularly to a surgical suction instrument that is used for suctioning fluids from a surgical site during a surgical procedure.

BACKGROUND ART

It is typically necessary to suction fluids, such as blood, from a surgical site during the course of a surgical procedure. The fluid is suctioned from the surgical site through a suction mechanism including a suction tube attached at one end to an instrument suction tube fitting provided at the top end of the handle of a surgical suction instrument having a surgical cavity insertion tube portion with an upper suction tube end connected to a bottom end of the handle and a lower suction tube tip end provided opposite the instrument suction tube fitting with a suction intake opening. The suction intake opening is in airflow connection with the instrument suction tube fitting through a suction passageway provided through the handle and the surgical cavity insertion tube portion. The suction fluid thus flows through the suction tube and the handle of the surgical suction instrument to a suction tube connected at the top end of the handle. It has been found through experience by the inventor hereof that the attachment of the suction tube to the top end of the handle hinders the maneuverability of the surgical suction instrument causing delays in positioning the suction intake opening at the required location by the user to suction fluids away from the bodily structures in the surgical area through which the surgeon is cutting or stitching. In addition, it is also necessary during most surgical procedures that fluids not only be suctioned, but that they be rapidly suctioned away as the cutting or incising is occurring so that as an incision is performed, the surgeon can immediately visualize particular body parts within the surgical site in order to prevent damage to organs, nerve bundles and the like. Any hindrance or slowness in the positioning and/or movement of the suction intake opening of the surgical suction instrument along the incision path as it is being made, may have grave consequences, particularly for those individuals having nerve bundles and other bodily glands and organs that are anatomically out of place and which are not expected to be within the surgical area. Should the surgeon be unable to visualize the cutting zone, even for a second or two because of a hindrance up in the movement and/or positioning of the suction intake opening by an assistant, the surgeon is unable to stop the smooth movement of the scalpel in time to prevent the irreparable severing of nerves and damage to other bodily structures. It is, therefore, not only desirable, but imperative that a surgical suction instrument be provided that eliminates the hindering effects of placing the handle of the surgical suction instrument between the top end of the handle and the suction intake opening. It would be beneficial, therefore, in order to increase the maneuverability of the suction intake opening of the surgical suction instrument to provide a surgical suction instrument having a suction tube attachment fitting located below the bottom of the handle so that the user is provided with the mechanical advantage of pivoting the surgical cavity insertion tube portion to position the suction intake opening from a point below the handle of the surgical suction instrument.

Another disadvantage of known surgical suction instruments is the surgical cavity inset tube portion has a fixed shape and is rigidly affixed to the handle. This configuration has the result that the assistant maneuvering the surgical suction instrument is required to be positioned within small, virtually predetermined area, with respect to the suction or surgical site. This limitation can cause the surgeon to be positioned in an unfavorable position as a compromise to the limitations of the surgical suction instrument. Because the surgical and/or suction site of course often changes during the course of an operation, delays are often encountered as the surgical team is repositioned. It would therefore also be desirable to have a surgical suction instrument that included a user positionable surgical cavity insertion tube portion adjustment mechanism provided between the handle and the top end of the surgical cavity insertion tube portion to allow the assistant to rapidly reconfigure the position of the suction intake opening with respect to the handle so as to minimize delays and repositioning of the surgical team during a surgical procedure.

Additionally, the use of a single suction intake opening can lead to damaged tissues and delays in suctioning fluids when the single suction intake becomes suction mounted to tissue surfaces, thereby, blocking the suction intake opening preventing fluids from being immediately drawn in and causing high vacuums to be pulled against the suction mounted tissue(s). As neither of these conditions is desirable, it would be a still further benefit to have a surgical suction instrument as described that further included multiple suction intake openings positioned through the bottom and bottom side surfaces of the lower suction tube tip end to minimize and/or eliminate the occurrence of suction mounting of the surgical suction instrument during a surgical procedure.

GENERAL SUMMARY DISCUSSION OF INVENTION

It is thus an object of the invention to provide a surgical suction instrument that includes a handle, a surgical cavity insertion tube, a suction tube attachment fitting, and a user positionable surgical cavity insertion tube adjustment mechanism; the instrument suction tube fitting have an exterior surface adapted for seating into the opening of a length of flexible surgical suction tube and a fitting passageway formed entirely therethrough into fluid communication with the surgical cavity insertion tube through an adjustment mechanism fluid passageway formed through the user positionable surgical cavity insertion tube adjustment mechanism; the surgical cavity insertion tube having an upper suction tube end in rigid connection with a bottom end of the surgical cavity insertion tube adjustment mechanism, the adjustment mechanism fluid passageway being in fluid communication with an upper suction tube opening defined by the upper suction tube end and in connection with a tube passageway formed through the surgical cavity insertion tube; the surgical cavity insertion tube terminating at a lower suction tube tip end in multiple suction intake openings formed through the bottom and bottom side surfaces of the lower suction tube tip end and each in fluid communication with the tube passageway; the surgical cavity insertion tube adjustment mechanism having a top section formed of rigid plastic and having a connection passageway section of the adjustment mechanism fluid passageway formed therethrough in fluid communication with the fitting passageway of the instrument suction tube fitting and a handle connection portion integrally formed with the handle at a location above the instrument suction tube fitting; the user positionable surgical cavity insertion tube adjustment mechanism including a number of sequentially connected, expandable, accordion fold sections that are each individually bendable by a user into mechanically stable half-expanded, fully-expanded and fully-collapsed conditions to allow a user to reconfigure the positions of the multiple suction intake openings formed through the lower suction tube tip end with respect to the handle. The term "mechanically stable" as used herein means that each accordion fold section remains in the condition in which it is placed by the user during normal working conditions until and unless it is reconfigured by the user during the surgical procedure.

Accordingly, a surgical suction instrument is provided. The surgical suction instrument includes a handle, a surgical cavity insertion tube, and a suction tube attachment fitting; the suction tube attachment fitting being in connection with the surgical cavity insertion tube at a location below a mechanical connection of the surgical cavity insertion tube and the handle.

In a preferred embodiment, the surgical cavity insertion tube terminates at a lower suction tube tip end in multiple suction intake openings formed through the bottom and bottom side surfaces of the lower suction tube tip end and each in fluid communication with a tube passageway thereof.

In another preferred embodiment, the surgical suction instrument further includes a surgical cavity insertion tube adjustment mechanism in connection between the handle and the surgical cavity insertion tube.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 3 is a side plan view showing one of the number of sequentially connected, expandable, accordion fold sections bent into the half-expanded condition.

FIG. 4 is a side plan view showing one of the number of sequentially connected, expandable, accordion fold sections bent into the fully-expanded condition.

FIG. 5 is a side plan view showing one of the number of sequentially connected, expandable, accordion fold sections bent into the fully-collapsed condition.

EXEMPLARY MODE FOR CARRYING OUT THE INVENTION

Figure 1:
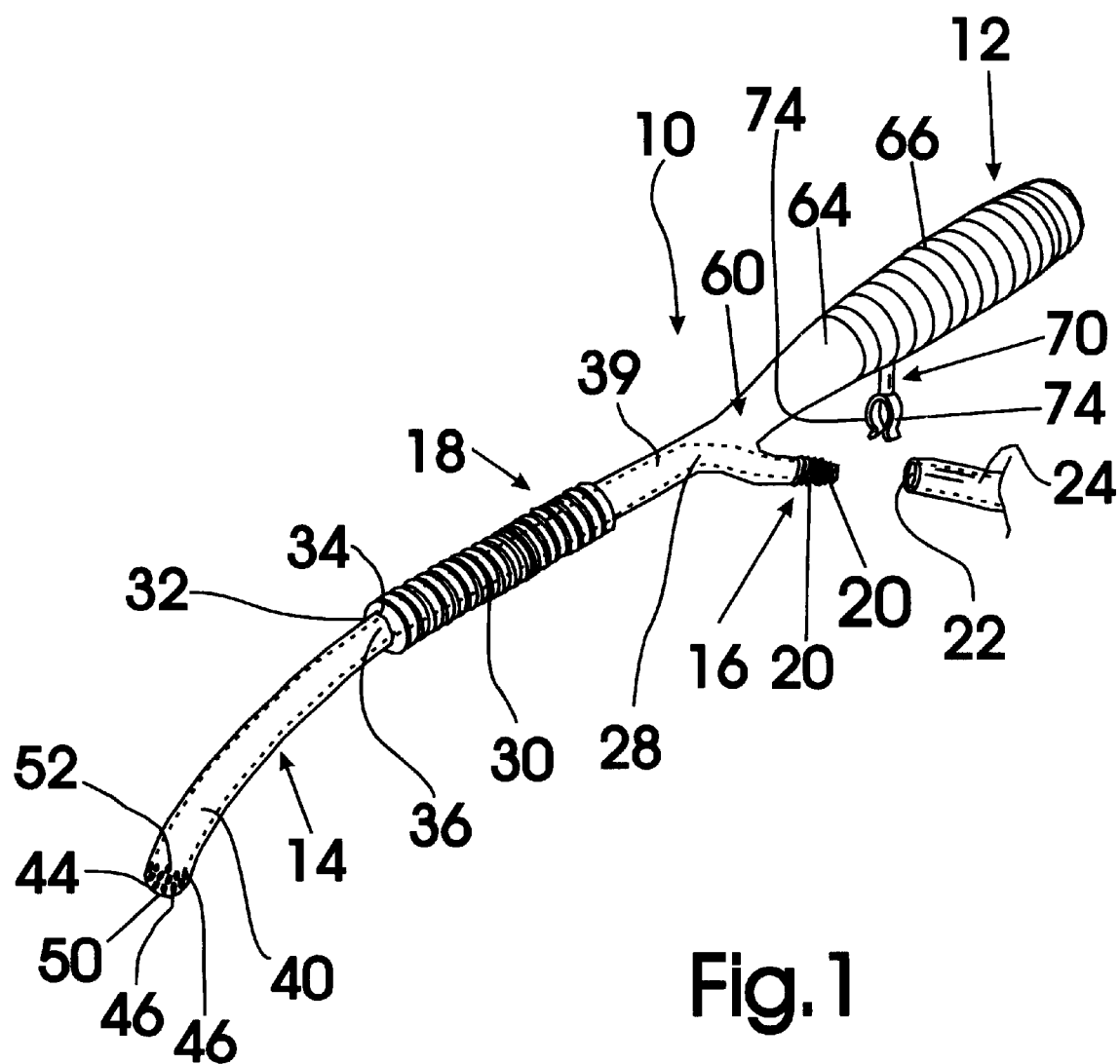
FIG. 1 is a perspective view of an exemplary embodiment of the surgical suction instrument of the present invention with an end of a representative length of flexible surgical suction tube positioned adjacent to the instrument suction tube fitting and an optional surgical suction tube attachment clip extending away from the handle.

FIGS. 1–5 show various exemplary embodiments of the surgical suction instrument of the present invention generally designated 10. Surgical suction instrument 10 includes a handle, generally designated 12; a surgical cavity insertion tube, generally designated 14; a suction tube attachment fitting, generally designated 16; and a user positionable surgical cavity insertion tube adjustment mechanism, generally designated 18.

Instrument suction tube fitting 16 has circumferential, exterior surface rings 20 adapted for seating into the opening 22 of a length of flexible surgical suction tube 24 and a fitting passageway 28 (shown in dashed lines) formed entirely therethrough. Fitting passageway 28 is in fluid communication with an adjustment mechanism fluid passageway 30 (shown in dashed lines) formed through user positionable surgical cavity insertion tube adjustment mechanism 18 via a connection passageway section 39 (shown in dashed lines) of adjustment mechanism fluid passageway 30.

Surgical cavity insertion tube 14 has an upper suction tube end 32 in rigid connection with a bottom end 34 of surgical cavity insertion tube adjustment mechanism 18. Adjustment mechanism fluid passageway 30 is in fluid communication with an upper suction tube opening 36 (shown in dashed lines) defined by the upper suction tube end 32 and in connection with a tube passageway 40 (shown in dashed lines) formed through surgical cavity insertion tube 14. Surgical cavity insertion tube 14 terminates at a lower suction tube tip end 44 in multiple, elliptically-shaped, suction intake openings 46 formed through the bottom 50 and bottom side surfaces 52 of lower suction tube tip end 44. Each of the suction intake openings 46 is in fluid communication with tube passageway 40 and consequently fitting passageway 28 through adjustment mechanism fluid passageway 30 (shown in dashed lines) including connection passageway section 39.

Figure 2:
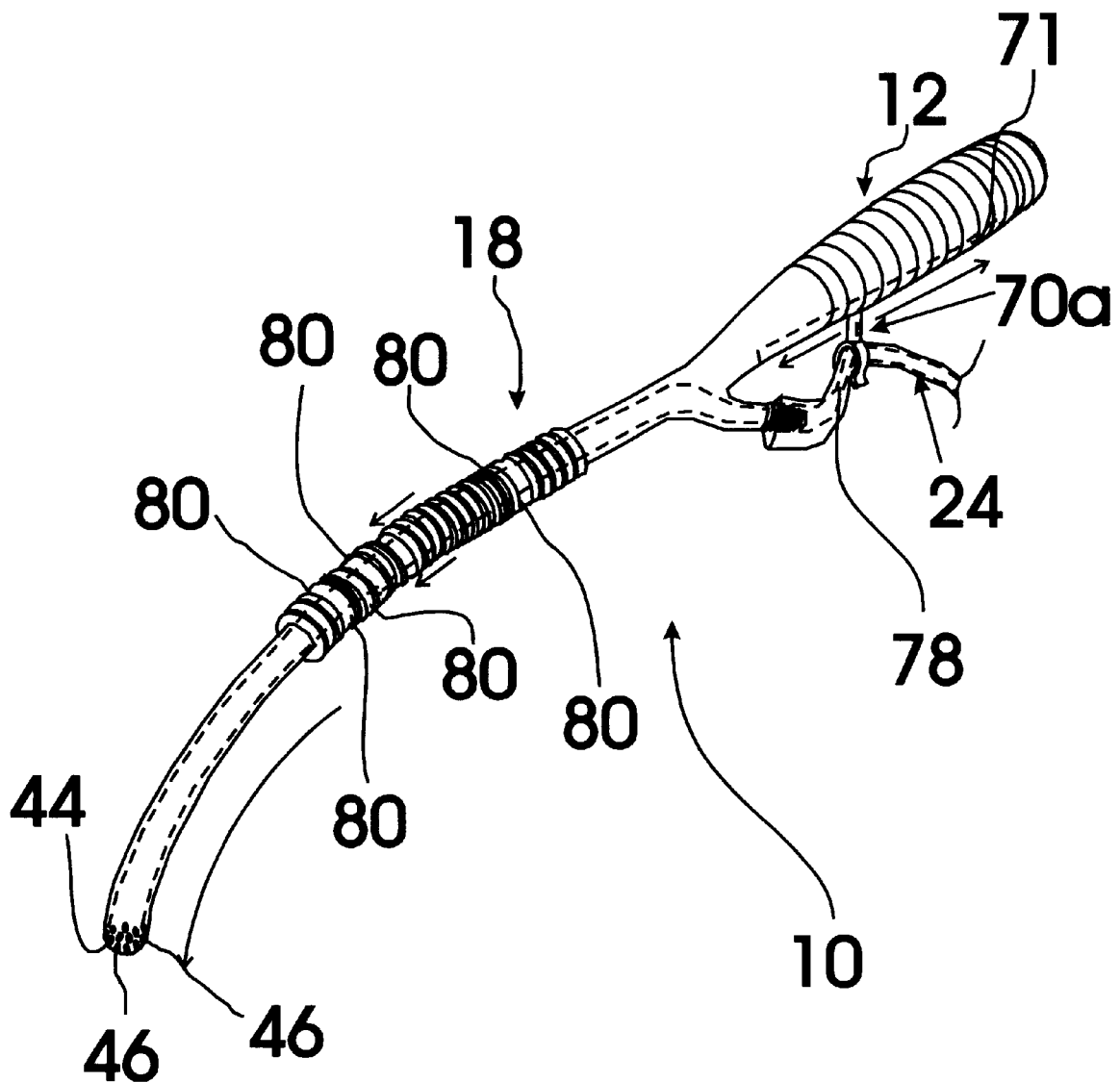
FIG. 2 is a perspective view of the exemplary surgical suction instrument of FIG. 1 with an end of a length of flexible surgical suction tube positioned onto the instrument suction tube fitting and section of the flexible surgical suction tube gripped between the two resilient clip members of the optional surgical suction tube attachment clip.

In this embodiment, surgical cavity insertion tube adjustment mechanism 18 has a top section, generally designated 60, formed of rigid plastic. Top section 60 has connection passageway section 39 of adjustment mechanism fluid passageway 30 formed therethrough in fluid communication with fitting passageway 28 of instrument suction tube fitting 16 and a handle connection portion 64 integrally formed with handle 12 at a location above instrument suction tube fitting 16. The phrase "above instrument suction tube fitting" means the instrument suction tube fitting is positioned between the bottom hand end 66 and the multiple suction intake openings 46. Handle 12 is provided with an optional surgical suction tube attachment clip, generally designated 70, in this embodiment. Surgical suction tube attachment clip 70 extends away from handle 12 and includes two resilient clip members 74 between which a user can secure a section 78 of flexible surgical suction tube 24 if desired. Surgical suction tube attachment clip 70 is provided to allow the user to modify the effective location of the attachment between the surgical suction instrument 12 and the flexible suction tube 24 in cases where such a modification would be desirable. As shown in FIG. 2, in this embodiment surgical suction tube attachment clip 70a is optionally connected in a manner such that it slides along a trackway 71 (shown in dashed lines) formed within and along handle 12 to allow a user to adjust its location as desired.

In this embodiment, user positionable surgical cavity insertion tube adjustment mechanism 18 including a number of sequentially connected, expandable, accordion fold sections 80 (not all numbered) that are each individually bendable by a user into a mechanically stable half-expanded condition 80a (FIG. 3), fully-expanded condition 80b (FIG. 4) and fully-collapsed condition 80c (FIG. 5) to allow a user to reconfigure the positions of the multiple suction intake openings 46 formed through the lower suction tube tip end 44 with respect to handle 12. The half-expanded condition is used to add curvature to user positionable surgical cavity insertion tube adjustment mechanism 18. The fully-expanded and fully-collapsed conditions are used, respectively to add or subtract length from user positionable surgical cavity insertion tube adjustment mechanism 18.

It can be seen from the preceding description that a surgical suction instrument has been provided.

It is noted that the embodiment of the surgical suction instrument described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A surgical suction instrument comprising:

a handle;

a surgical cavity insertion tube;

a suction tube attachment fitting; and a user positionable surgical cavity insertion tube adjustment mechanism;

said suction tube fitting having an exterior surface adapted for seating into an opening of a length of flexible surgical suction tube and a fitting passageway formed entirely therethrough into fluid communication with said surgical cavity insertion tube through an adjustment mechanism fluid passageway formed through said user positionable surgical cavity insertion tube adjustment mechanism;

said surgical cavity insertion tube having an upper suction tube end in rigid connection with a bottom end of said surgical cavity insertion tube adjustment mechanism, said adjustment mechanism fluid passageway being in fluid communication with an upper suction tube opening defined by said upper suction tube end and in connection with a tube passageway formed through said surgical cavity insertion tube;

said surgical cavity insertion tube terminating at a lower suction tube tip end in multiple suction intake openings formed through bottom and bottom side surfaces of said lower suction tube tip end and each in fluid communication with said tube passageway;

said surgical cavity insertion tube adjustment mechanism having a top section formed of rigid plastic and having a connection passageway section of said adjustment mechanism fluid passageway formed therethrough in fluid communication with said fitting passageway of said instrument suction tube fitting and a handle connection portion integrally formed with said handle at a location above said suction tube attachment fitting;

said user positionable surgical cavity insertion tube adjustment mechanism including a number of sequentially connected, expandable, accordion fold sections that are each individually bendable by a user into mechanically stable half-expanded, fully-expanded and fully-collapsed conditions to allow a user to reconfigure the positions of said multiple suction intake openings formed through said lower suction tube tip end with respect to said handle.

* * * * *